United States Patent
Scott

(10) Patent No.: US 7,959,590 B2
(45) Date of Patent: Jun. 14, 2011

(54) METHOD OF AND APPARATUS FOR PATELLA SUPPORT

(75) Inventor: John Scott, Dallas, TX (US)

(73) Assignee: New Options Sports, Dallas, TX (US)

( * ) Notice: Subject to any disclaimer, the term of this patent is extended or adjusted under 35 U.S.C. 154(b) by 333 days.

(21) Appl. No.: 12/105,982

(22) Filed: Apr. 18, 2008

(65) Prior Publication Data
US 2009/0156973 A1 Jun. 18, 2009

Related U.S. Application Data

(60) Provisional application No. 60/925,271, filed on Apr. 19, 2007.

(51) Int. Cl.
*A61F 5/00* (2006.01)
(52) U.S. Cl. ............................................. 602/23; 602/26
(58) Field of Classification Search ................... 602/23, 602/26–27; 128/882
See application file for complete search history.

(56) References Cited

U.S. PATENT DOCUMENTS

| | | | |
|---|---|---|---|
| 3,853,123 A * | 12/1974 | Moore | .............................. 602/26 |
| 4,494,534 A | 1/1985 | Hutson | |
| 4,856,501 A | 8/1989 | Castillo et al. | |
| 4,873,967 A | 10/1989 | Sutherland | |
| 4,941,462 A | 7/1990 | Lindberg | |
| 4,986,264 A | 1/1991 | Miller | |
| 5,024,216 A * | 6/1991 | Shiono | ............................ 602/26 |
| 5,277,697 A * | 1/1994 | France et al. | ................... 602/16 |
| 5,314,455 A | 5/1994 | Johnson, Jr. et al. | |
| 5,554,104 A | 9/1996 | Grim | |
| 5,562,605 A | 10/1996 | Taylor | |
| 5,624,389 A | 4/1997 | Zepf | |
| 5,741,220 A | 4/1998 | Brink | |
| 5,759,167 A | 6/1998 | Shields, Jr. et al. | |
| 5,810,752 A | 9/1998 | Grifka | |
| 5,865,776 A | 2/1999 | Springs | |
| 5,921,946 A | 7/1999 | Tillinghast et al. | |
| 6,066,110 A | 5/2000 | Nauert | |
| 6,117,164 A | 9/2000 | Gildersleeve et al. | |
| 2005/0020951 A1 | 1/2005 | Gaylord et al. | |
| 2006/0264793 A1 * | 11/2006 | Simmons et al. | ................ 602/23 |
| 2008/0139985 A1 * | 6/2008 | Gilmour | ........................ 602/26 |
| 2008/0300524 A1 * | 12/2008 | Scott | .............................. 602/26 |

* cited by examiner

*Primary Examiner* — Michael A. Brown
(74) *Attorney, Agent, or Firm* — Winstead PC

(57) ABSTRACT

A patella stabilization system having a unitary patella stabilizer sleeve extending at both ends into a plurality of straps for securing the patella stabilizer sleeve around a knee region and an upper inner strap extending from a first upper end of the patella stabilizer sleeve and an upper outer strap extending from a second upper end of the patella stabilizer sleeve, the upper outer strap comprising a fastener at a distal end of the upper outer strap. The system further includes a lower inner strap extending from a first lower end of the patella stabilizer sleeve and a lower outer strap extending from a second lower end of the patella stabilizer sleeve, the lower outer strap comprising a fastener at a distal end of the lower outer strap, a plurality of slots around a patella opening, and a buttress comprising a plurality of straps adapted to be adjustably positioned on an inside surface of the patella stabilizer band around a location on a circumferential edge of the patella opening.

19 Claims, 10 Drawing Sheets

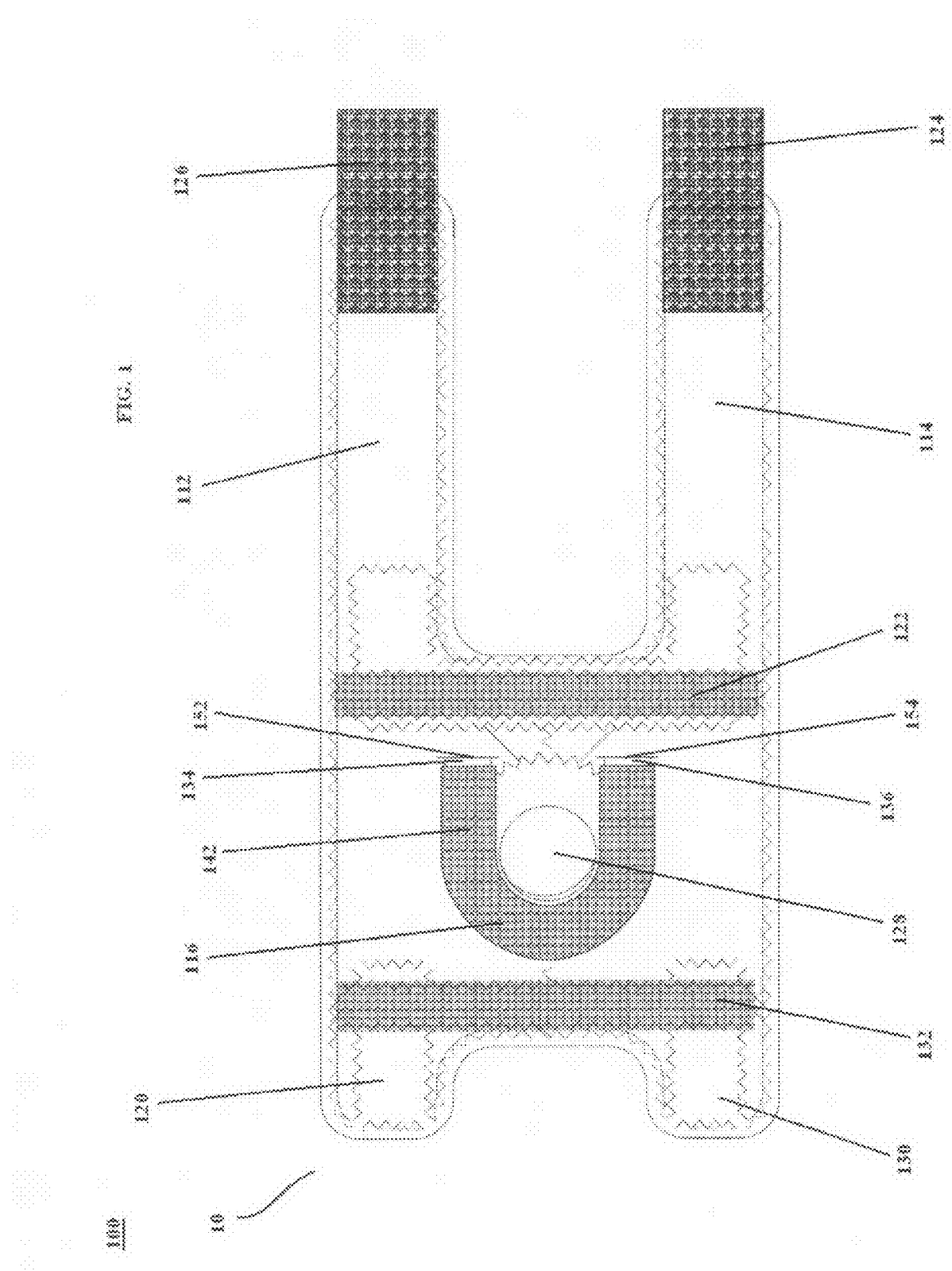

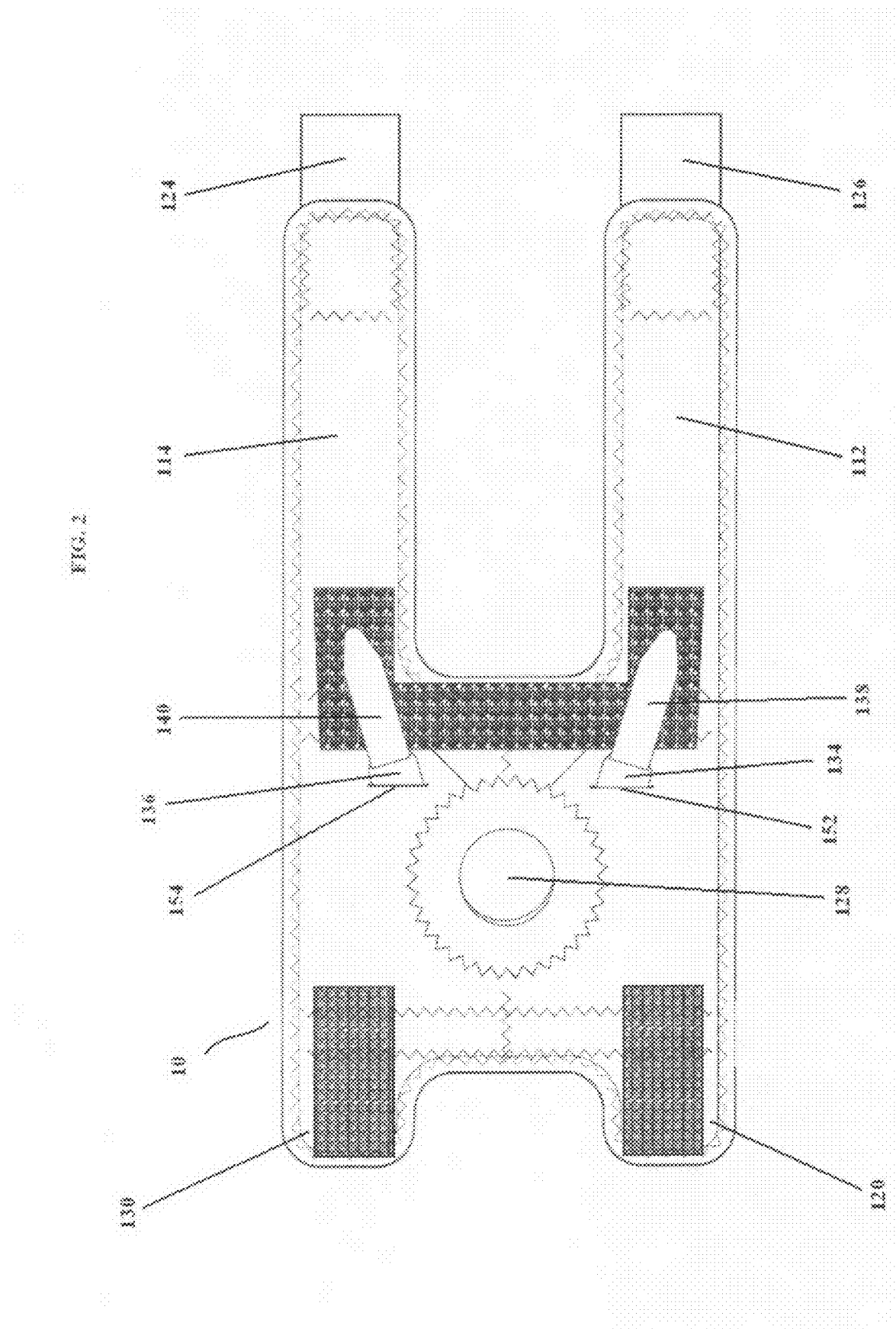

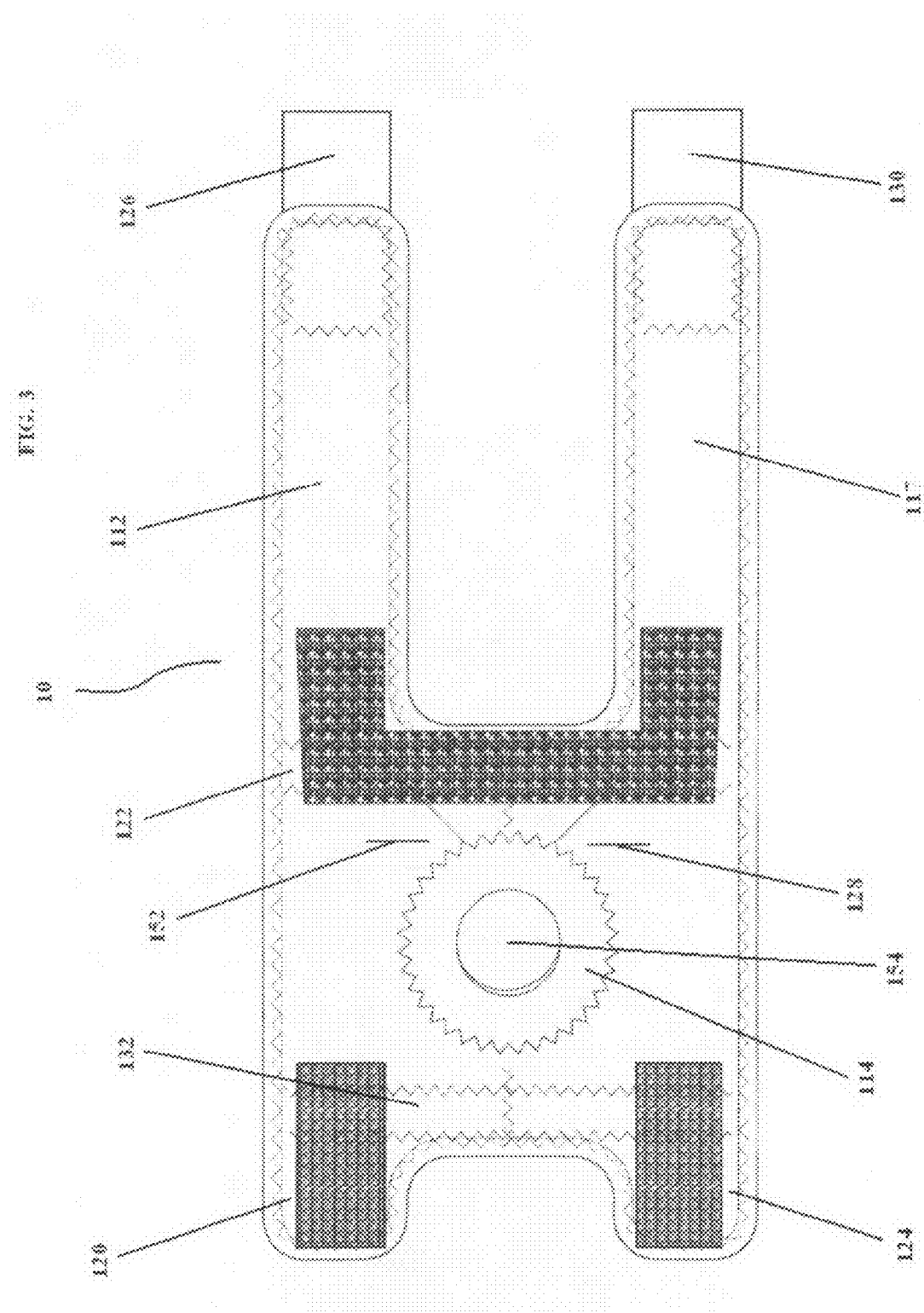

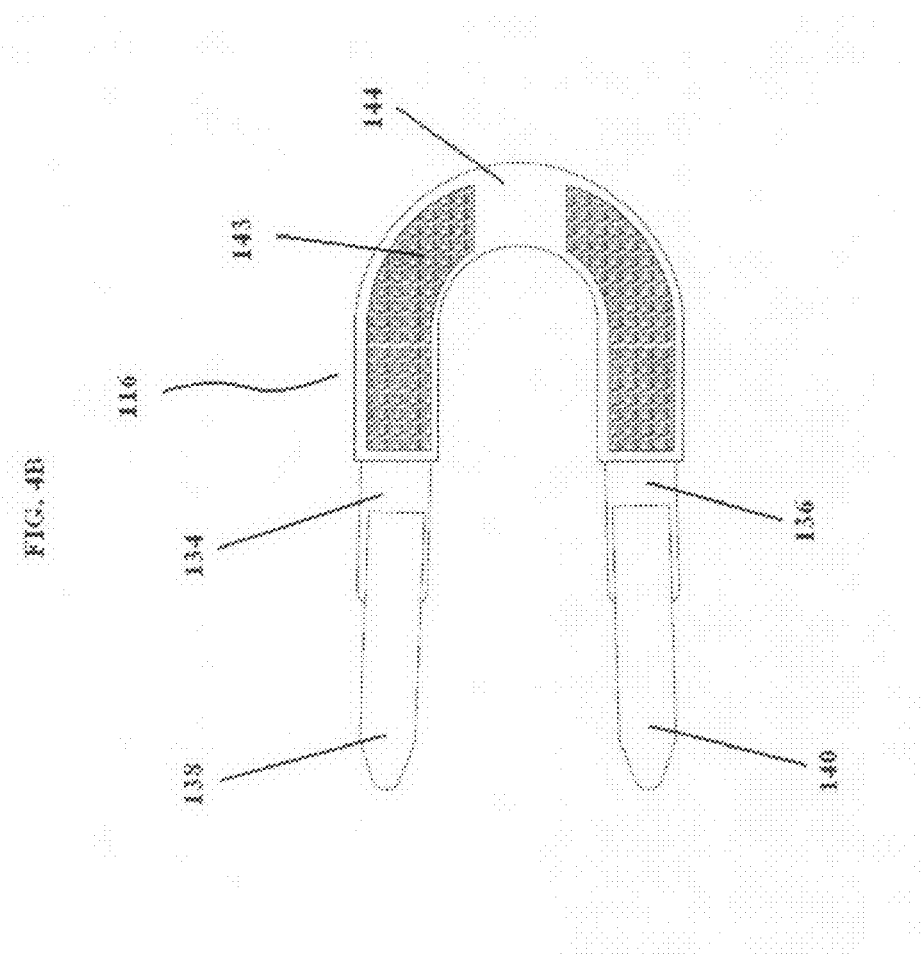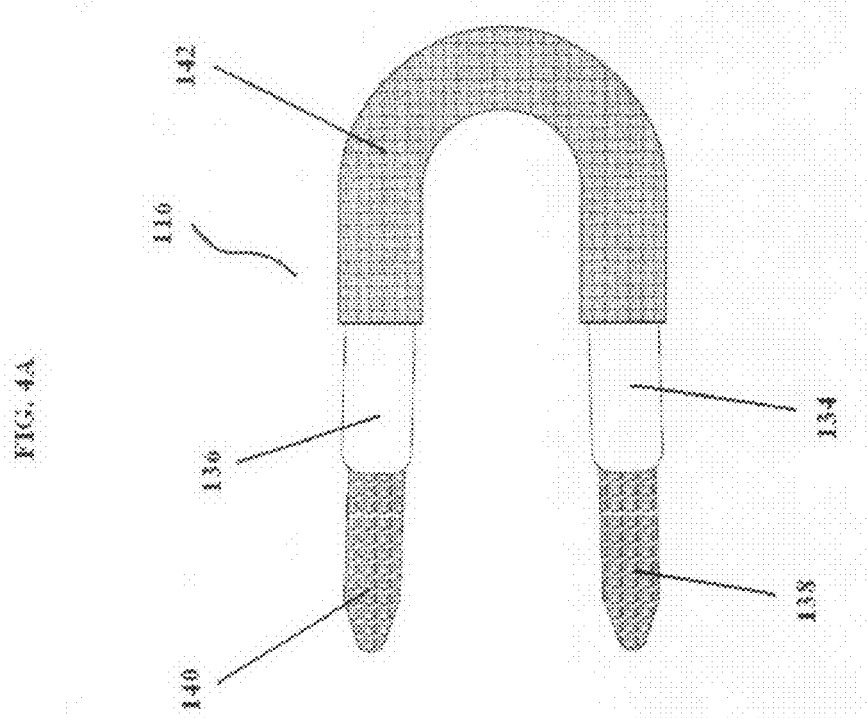

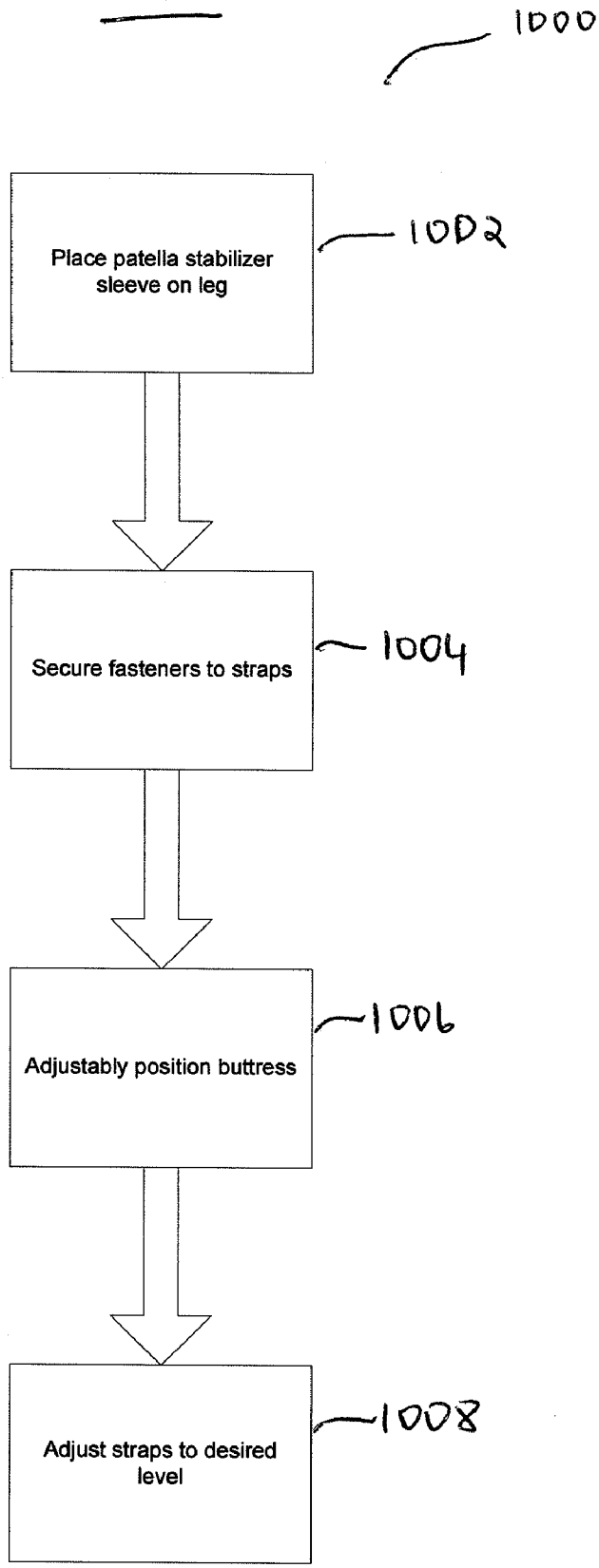

METHOD OF AND APPARATUS FOR PATELLA SUPPORT

CROSS-REFERENCE TO RELATED APPLICATIONS

This application claims priority from and incorporates by reference the entire disclosure of U.S. Provisional Patent Application Ser. No. 60/925,271, which was filed on Apr. 19, 2007.

BACKGROUND OF THE INVENTION

1. Field of Invention

The present invention relates to the field of orthopedic supports and, more particularly, but not by way of limitation, to an orthopedic support, system and method for supporting a knee and having a buttress that may be adjustably positioned to properly align and stabilize a user's patella.

2. History of Related Art

It is common in the Sports Medicine Industry to utilize orthopedic supports for various body parts subject to injury. The most common support areas include the knees, elbows, and ankles. Often injuries to these areas of the body can be treated by the utilization of an appropriate orthopedic support. In the event of surgery, rehabilitation is sometimes augmented by the utilization of such supports.

The design of orthopedic supports has changed considerably over the past two decades. The types of material used as well as the fastening and hinging mechanisms associated with orthopedic supports have been the subject of considerable study and improvement. One critical issue is the alignment and securement of elements of the affected joint. No joint is more susceptible to injury than the knee/patella joint.

For example, U.S. Pat. No. 4,986,264 to Miller, teaches a knee brace having an interior tibial shell and an interior femoral which are closely configured to the shape of the lower leg and thigh respectively and which are joined by a frame in the form of a pair of polycentric hinge joints. U.S. Pat. No. 4,856,501 to Castill et. al. teaches a knee brace having adjustable width frame pivoted to cuffs. The brace as set forth therein includes first and second frame members disposed on opposite sides of the joint to be supported, and first and second hinge members disposed substantially adjacent to joint and connected to the frame members to pivot the frame members about the joint.

Another example of related art is shown in U.S. Pat. No. 4,494,534 to Hudson. This patent teaches a universal leg brace system for controlling the degree of motion permitted by wearer's knee characterized by respective flexible sheets of cushioned material adapted for snugly wrapping around the wearer's thigh and calf. U.S. Pat. No. 5,554,104 to Grim likewise teaches a custom formed knee brace. This brace is taught to support weakened or injured knees by having formed components which conform to the unique configuration of an individual's leg surfaces. Other references include U.S. Pat. No. 6,066,110 to Nauert; U.S. Pat. No. 5,810,752 to Grifka; U.S. Pat. No. 5,624,389 to Zepf; U.S. Pat. No. 4,873,967 to Sutherland; U.S. Pat. No. 5,921,946 to Tillinghas; and U.S. Pat. No. 5,562,605 to Taylor.

As seen from the patents listed above, the aspect of joint support, flexibility, and rehabilitation have received considerable attention in prior orthopedic support design. One area of continued concern is, however, the adaptability of a single orthopedic support for a knee that is adapted to provide a desired pressure on the user's knee in order to properly align and support a user's patella.

For the aforementioned reasons, there is a need in the art for an orthopedic support, system and method for a knee that overcomes these limitations to provide a new level of flexibility and customizability.

SUMMARY OF THE INVENTION

A patella stabilization system for a user's leg. The system includes a unitary patella stabilizer sleeve extending at both ends into a plurality of straps for securing the patella stabilizer sleeve around a knee region and an upper inner strap extending from a first upper end of the patella stabilizer sleeve and an upper outer strap extending from a second upper end of the patella stabilizer sleeve, the upper outer strap comprising a fastener at a distal end of the upper outer strap. The system further includes a lower inner strap extending from a first lower end of the patella stabilizer sleeve and a lower outer strap extending from a second lower end of the patella stabilizer sleeve, the lower outer strap comprising a fastener at a distal end of the lower outer strap, a plurality of slots around a patella opening, and a buttress comprising a plurality of straps adapted to be adjustably positioned on an inside surface of the patella stabilizer band around a location on a circumferential edge of the patella opening for properly aligning a user's patella.

A unitary hinged knee support apparatus adapted to accommodate a leg portion of a user. The apparatus includes a sleeve extended at both ends into a plurality of straps, a patella opening, and an upper fastener assembly having an upper inner strap extended from a first upper end of the apparatus and an upper outer strap extended from a second upper end of the apparatus, the upper outer strap having a fastener at a distal end. The apparatus further includes a lower fastener assembly having a lower inner strap extended from a first lower end of the apparatus and a lower outer strap extended from a second lower end of the apparatus, the lower outer strap having a fastener at a distal end, a plurality of slots around a patella opening, and the apparatus adapted to receive a buttress comprising a plurality of straps, the buttress being adapted to be adjustably positioned on an inside surface of the apparatus around a location on a circumferential edge of the patella opening.

A method for properly aligning a user's patella. The method includes providing a unitary patella stabilizer sleeve having an upper fastener assembly comprising a first inner strap and a first outer strap and a lower fastener assembly comprising a second inner strap and a second outer strap, wrapping the inner straps around a back portion of a knee, wrapping the outer straps over the inner straps and around to a front portion of the knee, and securing, via the first inner and outer straps of the upper fastener assembly, a thigh region of the user. The method further includes the step of securing, via the second inner and outer straps of the lower fastener assembly, a calf region of the user and adjustably positioning, on an inside surface of the patella stabilizer around a location on a circumferential edge of a patella opening, a buttress comprising a plurality of straps for varying compression and alignment around the user's patella by increasing or decreasing tightness of the plurality of buttress straps.

BRIEF DESCRIPTION OF THE DRAWINGS

A more complete understanding of the system of the present invention may be obtained by reference to the following Detailed Description when taken in conjunction with the accompanying Drawings wherein:

FIG. 1 illustrates an inside view of a patella stabilization system in accordance with a preferred embodiment of the present invention;

FIG. 2 illustrates an outside view of the patella stabilization system of FIG. 1 in accordance with an embodiment of the present invention;

FIG. 3 illustrates an inside view of a patella stabilizer without a patella buttress in accordance with an embodiment of the present invention;

FIG. 4A illustrates a front view of a buttress of the patella stabilization system in accordance with an embodiment of the present invention;

FIG. 4B illustrates a back view of the buttress of the patella stabilization system in accordance with an embodiment of the present invention;

FIG. 10 illustrates a flow diagram of a method for using the patella stabilizer system in accordance with an embodiment of the present invention.

DETAILED DESCRIPTION OF THE INVENTION

Figure 5:
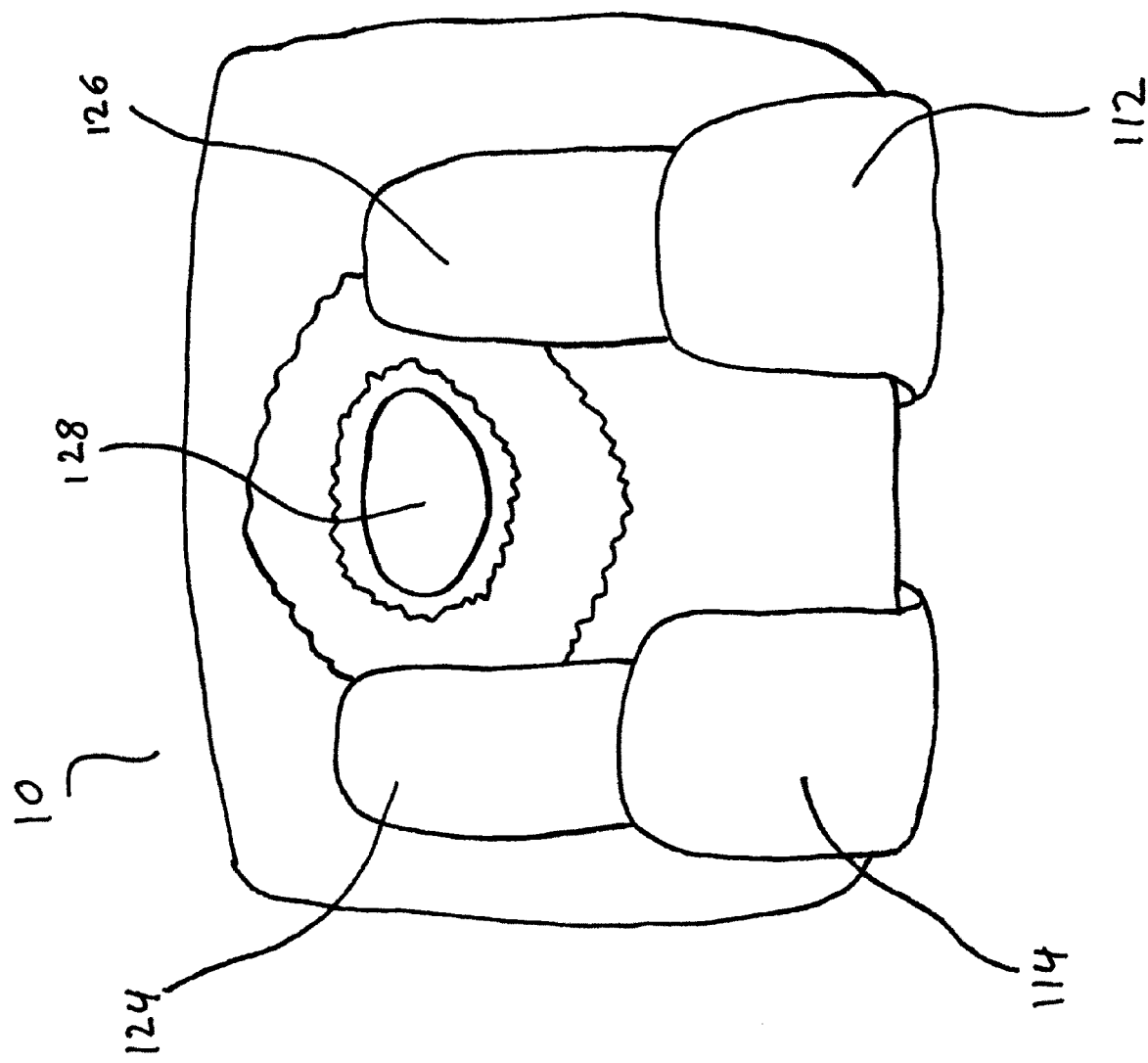
FIG. 5 illustrates a side perspective view of a closed patella stabilization system in accordance with an embodiment of the present invention.

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. For example, a particular feature, structure, or characteristic described herein in connection with one embodiment may be implemented within other embodiments without departing from the spirit and scope of the invention. In addition, it is to be understood that the location or arrangement of individual elements within each disclosed embodiment may be modified without departing from the spirit and scope of the invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views.

Referring first to FIG. 1, there is shown a preferred embodiment of a patella stabilization system 100 of the present invention. The patella stabilization system 100 comprises a unitary patella stabilizer sleeve 10 and a patella support buttress 116. Patella stabilizer sleeve 10 comprises an upper outer strap 112 having a fastener portion 126 and a lower outer strap 114 having a fastener portion 124. While only two straps are shown in FIG. 1, any number of straps may be used without departing from the spirit and scope of the present invention. Patella stabilizer sleeve 10 may be constructed using any natural or synthetic material, including both inelastic and elastic materials, having sufficient flexibility and resiliency to enable patella stabilizer sleeve 10 to anatomically conform to a body member to which it is applied. Patella stabilizer sleeve 10 may be formed of, for example, two-sided nylon Neoprene, which provides durability and elasticity. According to an exemplary embodiment, the two-sided nylon Neoprene has a thickness of approximately ⅛ inch, but any thickness may be used. The outside of patella stabilizer sleeve 10 may be constructed of unbroken loop (UBL) or Koolflex™ material. According to an exemplary embodiment, the body of upper and lower outer straps 112, 114, with the exception of fasteners 124 and 126 may be constructed using hook and pile portions to facilitate adjustability and ease of use by a user.

Still referring to FIG. 1, patella stabilizer sleeve 10 may include a patella opening 128 for added comfort. Upper and lower outer straps 112 and 114 comprise fastener portions 126 and 124 extending from distal ends. Once the patella stabilizer sleeve 10 is placed onto a user's leg and more particularly the knee area, an upper inner strap 120 and a lower inner strap 130 wrap around a back portion of the knee. For example, upper inner strap 120 is adapted to wrap around a lower portion of a thigh region and lower inner strap 130 is adapted to wrap around an upper calf portion of a user's leg. Upper and lower outer straps 112 and 114 are then wrapped over upper and lower inner straps 120 and 130, respectively, and fastener portions 126 and 124 are attached thereto. According to exemplary embodiments, fastener portions 126 and 124 may be constructed of hook and pile portions while upper and lower inner straps 120, 130 may contain loop material so that they may be secured against each other and to facilitate adjustability and ease of use by the user. Upper and lower outer straps 112 and 114, in conjunction with upper and lower inner straps 120 and 130, may be of sufficient length to encompass the thigh and calf regions at least once. Additionally, a space between upper and lower outer straps 112 and 114 and a space between upper and lower inner straps 120 and 130 provides for a popliteal opening 200 (shown in FIG. 7) when patella stabilizer sleeve 10 is secured around a user's knee. It will be appreciated that compression may be adjusted to a desired level by increasing or decreasing the tightness of upper and lower outer straps 112 and 114 around the thigh and calf regions.

Still referring to FIG. 1, a hinge 122 is distinctly placed along a medial portion of patella stabilizer sleeve 10. According to one embodiment, a first hinge 122 may be, for example, a spiral stay; however, in other embodiments, first hinge 122 may be a single axis hinge, a double axis hinge, a complex hinge, or any other structure that may help support a user's knee. As shown, first hinge 122 is an internal hinge and is held in place with stitching; however, first hinge 122 may also be an external hinge or other type of hinge for supporting a user's knee. A second hinge 132 is disposed opposite first hinge 122 and is positioned to run along an opposite side of a user's knee when patella stabilizer sleeve 10 is secured therearound. Stitching around second hinge 132 helps secure the hinge in place. Similar to first hinge 122, various embodiments of second hinge 132 are contemplated. Likewise, patella stabilizer sleeve 10 may contain one, both, or neither of first hinge 122 and second hinge 132.

Still referring to FIG. 1, the patella stabilizer system 100 further includes a patella support buttress 116. Buttress 116 is adapted to be placed on an inside surface of patella stabilizer sleeve 10 around a location on a circumferential edge of patella opening 128. Buttress 116 has a plurality of buttress straps 134 and 136. The body of buttress straps 134 and 136 may be constructed with hook-and-pile portions to facilitate adjustability. Buttress 116 includes a front side 142 and a back side 144 (not shown). According to one embodiment, front side 142 is made of a material that has grip characteristics to prevent slippage when placed against human skin such as, for example, shark skin material.

Patella stabilizer sleeve 10 includes at least two slots 152 and 154 around patella opening 128. Slots 152 and 154 are adapted to allow passage of buttress straps 134 and 136 for securement to an outside of patella stabilizer sleeve 10. According to one embodiment, an inside surface of patella stabilizer sleeve 10 around the circumferential edge of patella opening 128 may be constructed with loop portions to engage back side 144 of buttress 116 in order to facilitate securing buttress 116 to patella stabilizer sleeve 10. Buttress 116 may be adjustably positioned on the inside surface of patella stabilizer sleeve 10 around a location on the circumferential edge of patella opening 128 to provide a desired pressure and properly align a user's patella. According to one embodiment, buttress 116 can be positioned in a medial or lateral direction relative to a user's patella. Slots 152 and 154 may be positioned so that buttress 116 partially encircles a first portion of patella opening 128. For illustration purposes, only two slots 152 and 154 are shown; however, additional slots may be included so that buttress 116 may be positioned to partially encircle a second portion of patella opening 128. By including additional slots, buttress 116 can be utilized to support a user's patella from a plurality of directions depending on the specific needs of the user.

FIG. 2 illustrates an outside view of the patella stabilization system 100 of FIG. 1 in accordance with an embodiment of the present invention. As can be seen from this view, patella stabilizer sleeve 10 comprises slots 152 and 154 located to one side of patella opening 128. Buttress 116 (not shown) is placed around a portion of a circumferential edge of patella opening 128. Buttress straps 134 and 136 are passed through slots 152 and 154. Buttress 116 may be adjusted by a user by pulling buttress straps 134 and 136 further through slots 152 and 154 and securing the straps to an outside of patella stabilizer sleeve 10 with fasteners 138 and 140. Fasteners 138 and 140 may contain hook portions for fastening to the outside portion of patella stabilizer sleeve 10. In one embodiment of patella stabilization system 100, patella stabilizer sleeve 10 may be worn interchangeably on either a user's right knee and/or a user's left knee. Additionally, patella stabilizer sleeve 10 may be fitted on a user's knee in such a manner that lower outer strap 114 is adapted to be wrapped around a thigh portion when upper outer strap 112 is wrapped around a calf portion and may also be fitted on a user's knee in such a manner that lower outer strap 114 is adapted to be wrapped around a calf portion when upper outer strap 112 is wrapped around a thigh portion.

FIG. 3 illustrates an inside view of a patella stabilizer sleeve 10 without a buttress 116 in accordance with an embodiment of the present invention. From this view, it can be seen that patella stabilizer sleeve 10 contains a securement area 117 around a portion of patella opening 128. Securement area 117 may be a separate piece of material stitched in place or alternatively may be an area of patella stabilizer sleeve 10 adapted for buttress 116 to be attached to. A portion of securement area 117 may contain loop material so that buttress 116 may be placed over securement area 117 and the hook portion of buttress 116 may engage the loop portion for securing buttress 116 in place. Slots 152 and 154 are also seen through which straps 134 and 136 may be passed.

FIGS. 4A-4B illustrate front and back views of buttress 116 of patella stabilization system 100. Buttress 116 comprises a plurality of buttress straps 134 and 136 with buttress fasteners 138 and 140. The body of buttress straps 134 and 136, with the exception of buttress fasteners 138 and 140 may be constructed with hook-and-pile portions to facilitate adjustability and ease of use by the user. Buttress 116 includes front side 142 and back side 144 (shown in FIG. 4B). According to an exemplary embodiment, front side 142 is made of a material that has grip characteristics and prevents slippage when placed against human skin such as, for example, shark-skin. Back side 144 of buttress 116 may be constructed with hook-and-pile portions to facilitate adjustability and ease of use by the user. Buttress 116 is adapted to be placed on an inside surface of patella stabilizer sleeve 10 around a location on a circumferential edge of patella opening 128. According to an exemplary embodiment, buttress 116 is horse-shoe like in shape. However, buttress 116 may be of other shapes such that buttress 116 can be placed on an inside surface of patella stabilizer sleeve 10 around a location on a circumferential edge of patella opening 128 to provide a desired pressure and properly align the user's patella.

FIG. 5 is a side perspective view of a patella stabilization system 100 in closed configuration in accordance with an embodiment of the present invention. In the embodiment shown, fastener portions 124 and 126 are stitched to upper and lower outer straps 112 and 114. Fastener portions 124 and 126 may contain hook portions that may engage the UBL material of patella stabilizer sleeve 10. Other materials and ways of fastening the straps are contemplated, such as having upper and lower outer straps 112 and 114 loop through a D-ring attached to patella stabilizer sleeve 10 and then fastener portions 124 and 126 engaging the material of upper and lower outer straps 112 and 114.

Figure 6:
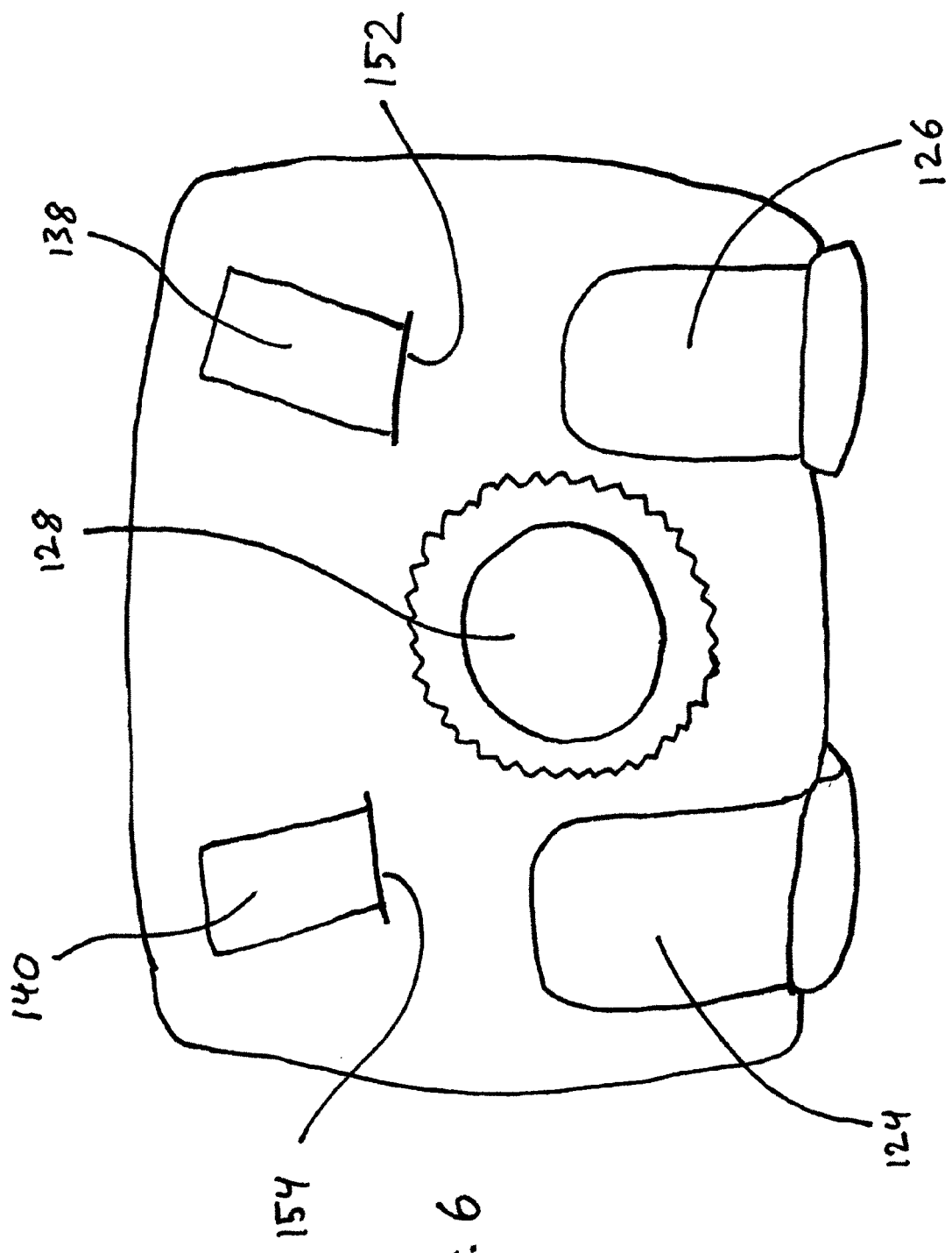
FIG. 6 illustrates a side perspective view of a closed patella stabilization system in accordance with an embodiment of the present invention.

FIG. 6 is a perspective view of patella stabilization system 100 as configured in FIG. 5, but from a slightly different angle. It can be seen that buttress fasteners 138 and 140 have been passed through slots 152 and 154. From this view, it can be seen that without having to remove patella stabilizer sleeve 10, a user may increase the pressure provided to the patella by buttress 116 by pulling buttress straps 134 and 136 further through slots 152 and 154 and then re-engaging the hook-and-pile portions of buttress fasteners 138 and 140 to patella stabilizer sleeve 10.

Figure 7:
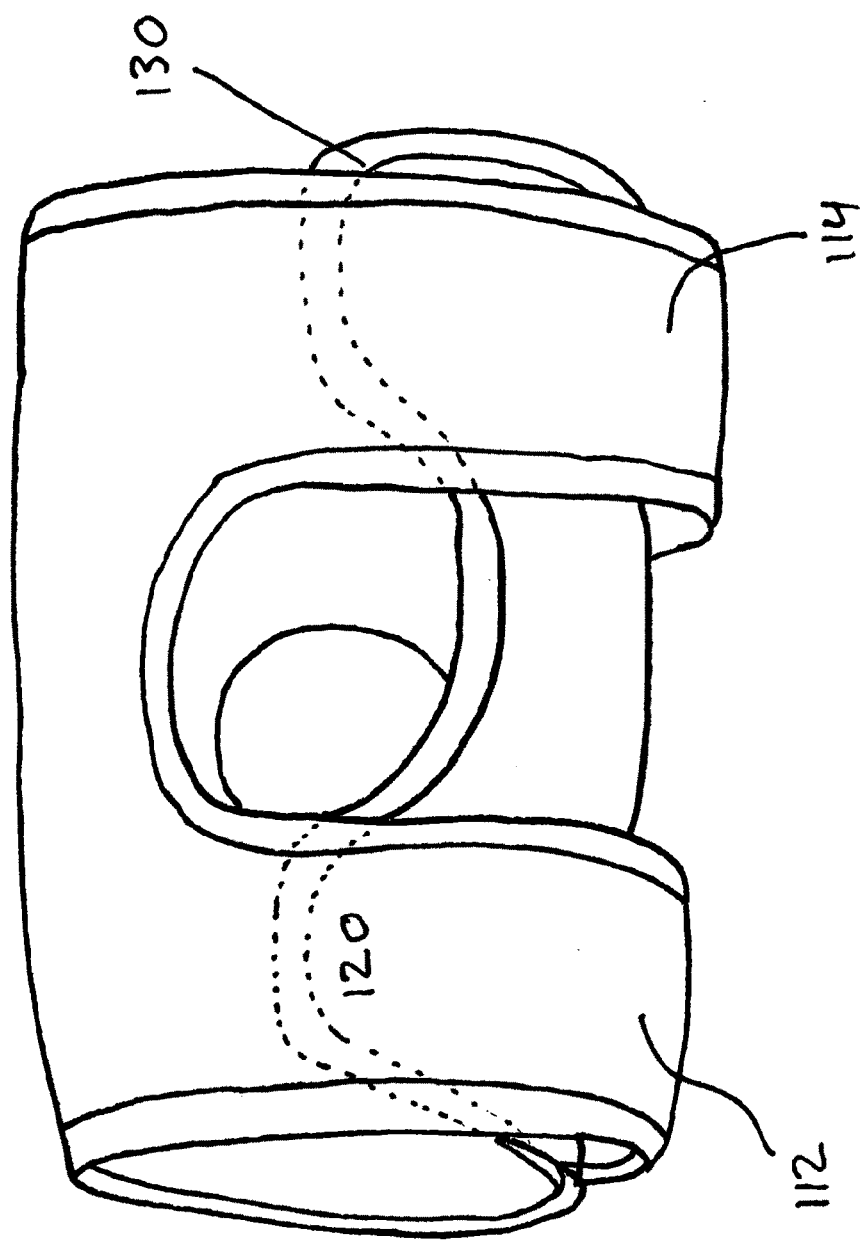
FIG. 7 illustrates a rear view of a closed patella stabilization system in accordance with an embodiment of the present invention.

FIG. 7 is a perspective view of patella stabilization system 100 as configured in FIG. 5, but from a back view. From this view, the popliteal opening 200 created by the intersection of outer straps 112 and 114 and inner straps 120 and 130 can be seen.

Figure 8:
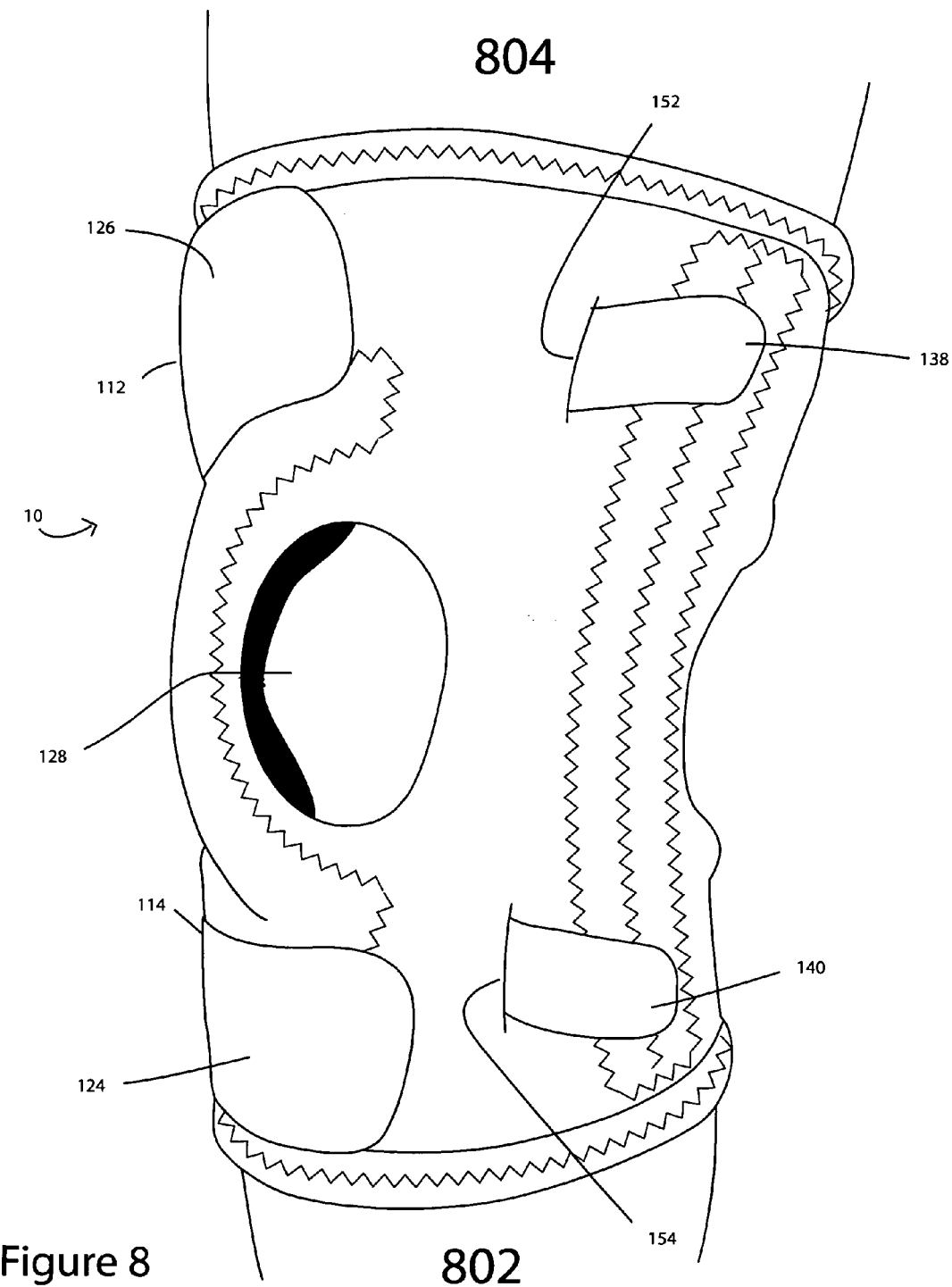
FIG. 8 illustrates a perspective view of a patella stabilization system placed on a user's leg in accordance with an embodiment of the present invention.

FIG. 8 is an illustration of patella stabilization system 100 on a user's leg. In operation, patella stabilizer sleeve 10 is adapted to be applied onto a user's leg such that lower strap 114 extends around a calf region 802 of the user while upper strap 112 is adapted to wrap around a thigh region 804 of the user. In one embodiment, patella stabilizer sleeve 10 is bi-directional such that upper strap 112 may secure either calf region 802 or thigh region 804. Likewise, lower strap 114 is adapted to wrap around either calf region 802 or thigh region 804. FIG. 8 further illustrates slots 152 and 154 which allows passage of buttress straps 134 and 136 and buttress fasteners 138 and 140 through for securement of buttress 116 to patella stabilizer sleeve 10. Buttress 116 is adapted to be placed on an inside surface of patella stabilizer sleeve 10 around a location on a circumferential edge of patella opening 128 and may be adjustably positioned to properly align a user's patella. It can be seen that buttress 116 along with buttress straps 134 and 136 form a generally "C" shape and that pulling buttress straps 134 and 136 further through slots 152 and 154 will move buttress 116 closer to patella opening 128 and properly align a user's patella.

Figure 9:
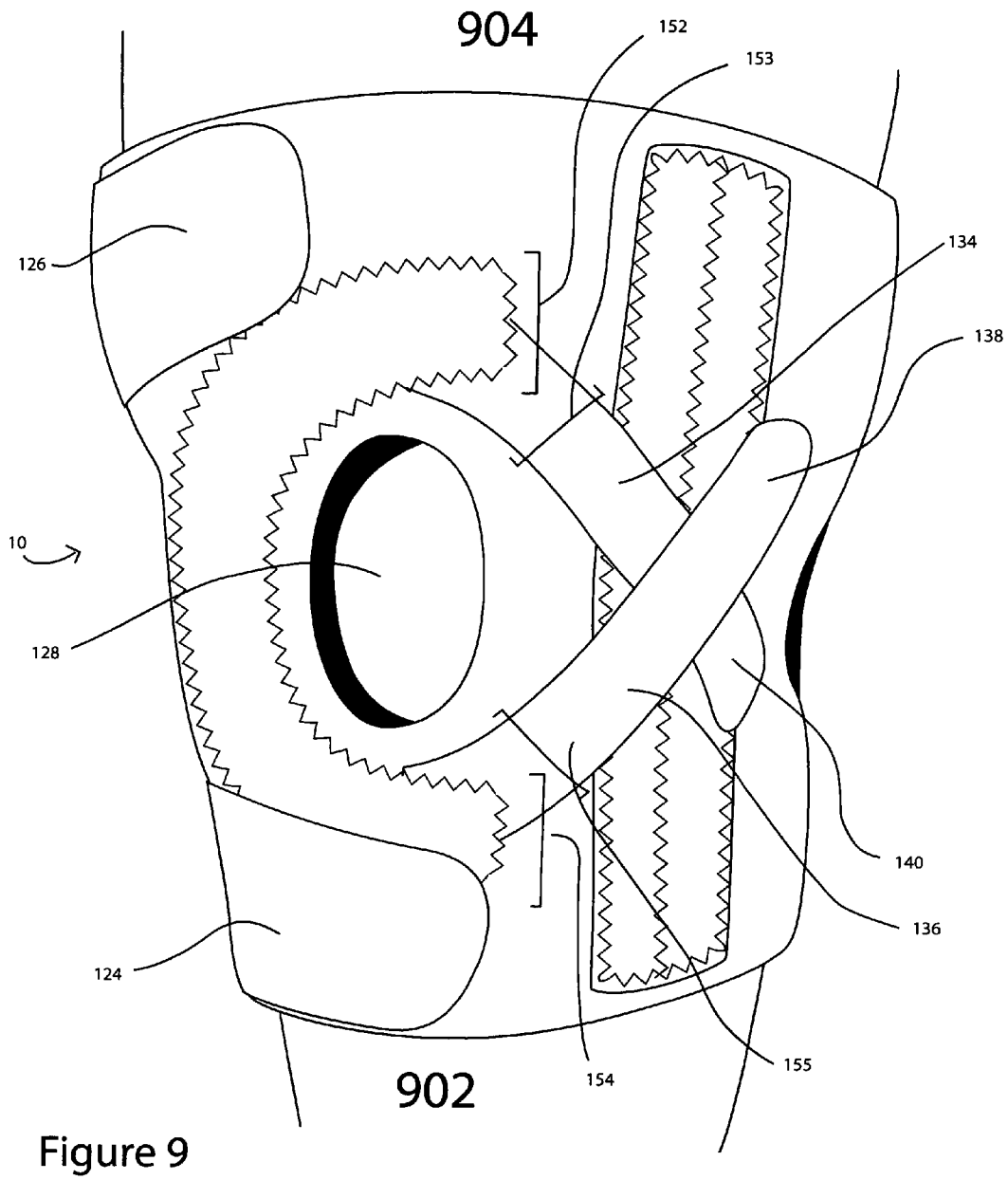
FIG. 9 illustrates a perspective view of a patella stabilization system placed on a user's leg in accordance with an alternate embodiment of the present invention.

In operation, patella stabilizer sleeve 10 is adapted to be applied onto a user's leg. FIG. 9 is thus a perspective view of the use of the patella stabilization system of the present invention wherein the patella stabilizer sleeve 10 is placed on a user's leg in accordance with an alternate embodiment of the present invention. In the embodiment shown, angled slots 153 and 155 can be seen for passing buttress straps 134 and 136 therethrough and attaching buttress fasteners 138 and 140 to patella stabilizer sleeve 10. Buttress 116 is adapted to be placed on an inside surface of patella stabilizer sleeve 10 around a location on a circumferential edge of patella opening 128 and may be adjustably positioned to properly align a user's patella. It can be seen that when buttress straps 134 and 136 are passed through angled non parallel slots 153 and 155, buttress straps 134 and 136, along with buttress fasteners 138 and 140 form a generally "X" shape. When buttress strap 136 is pulled in a generally outward and upward direction, the lower distal end of buttress 116 moves closer to patella opening 128. Likewise, when buttress strap 134 is pulled in a generally outward and downward direction, the upper distal end of buttress 116 moves closer to patella opening 128. In this manner, the radius of buttress 116 may be decreased so that buttress 116 more tightly encircles a user's patella and provide better compression to a user's patella. In the embodiment shown, buttress fastener 140 is laid on top of buttress fastener 138, however the straps can be attached in reverse order.

Referring now to FIG. 10, there is shown a flow diagram illustrating a method 1000 for using the patella stabilizer sleeve 10 according to an embodiment of the present invention. At step 1002, the user places the patella stabilizer sleeve 10 onto the user leg and more particularly the knee area. At step 1004, the patella stabilizer sleeve 10 is wrapped around the knee area by securing fasteners 124, 126 against the lower inner strap 130 and upper inner strap 120, respectively. At step 1006, buttress 116 is adjustably positioned on the inside surface of the patella stabilizer sleeve 10 around a location on the circumferential edge of the patella opening 128 to provide a desired pressure and properly align a user's patella. According to an exemplary embodiment, the buttress 116 can be positioned in a medial or lateral direction relative to the user's patella. At step 1008, the straps 112, 114, 120, 130, 138 and 140 are adjusted to a desired level by increasing or decreasing the tightness of the straps 112, 114, 120, 130, 138 and 140 around the thigh region, the calf region and the patella region, respectively.

It should be noted that the terms "hook-and-pile fasteners" and "hook-and-loop fasteners" refer to a recognized structure which is often sold under the trademark Velcro®, and that the hook material and the pile or loop material engage one another. In addition, various surface designs, patterns, and colors may be used as well as various thicknesses of neoprene. Likewise, various embodiments are not limited to the use of neoprene, as other materials may prove satisfactory in their use as patella stabilizers. The size and shape of the brace along with the buttress as shown herein is an exemplary embodiment and other cutout shapes and clearance designs may be utilized in order to accommodate various leg sizes.

Although various embodiments of the patella stabilizer system have been illustrated in the accompanying Drawings and described in the foregoing Detailed Description, it will be understood that the invention is not limited to the embodiments disclosed, but is capable of numerous rearrangements, modifications, and substitutions without departing from the spirit of the invention as set forth herein.

What is claimed is:

1. A patella stabilization system for a user's leg, the system comprising:
    a unitary patella stabilizer sleeve extending at both ends into a plurality of straps for securing the patella stabilizer sleeve around a knee region;
    an upper inner strap extending from a first upper end of the patella stabilizer sleeve and an upper outer strap extending from a second upper end of the patella stabilizer sleeve, the upper outer strap comprising a fastener at a distal end of the upper outer strap;
    a lower inner strap extending from a first lower end of the patella stabilizer sleeve and a lower outer strap extending from a second lower end of the patella stabilizer sleeve, the lower outer strap comprising a fastener at a distal end of the lower outer strap;
    a pair of slots extending substantially non-parallel to a patella opening;
    a buttress comprising an upper strap and a lower strap operable to be adjustably positioned on an inside surface of the patella stabilizer sleeve around a location on a circumferential edge of the patella opening; and
    wherein the upper strap is operable to be pulled in a generally outward and downward direction causing an upper distal end of the buttress to move closer to the patella opening and the lower strap is operable to be pulled in a generally outward and upward direction causing a lower distal end of the buttress to move closer to the patella opening for properly aligning a user's patella.

2. The system of claim 1, wherein the upper and lower inner straps wrap around a back portion of the knee and the upper and lower outer straps wrap over the upper and lower inner straps and around to a front portion above and below the knee.

3. The system of claim 1, wherein the patella stabilizer sleeve is symmetrical and bi-directional such that the upper and lower inner straps and the upper and lower outer straps are identical and their orientation interchangeable when the patella stabilizer sleeve is in use.

4. The system of claim 1, wherein the upper and lower buttress straps are adapted to properly align a user's patella by allowing non parallel passage of the upper and lower buttress straps through the pair of slots around the patella opening such that the buttress and the upper and lower buttress straps form a C-shape structure for providing stability and proper alignment of the user's patella.

5. The system of claim 1, wherein the upper and lower buttress straps are adapted to vary compression around the user's patella by allowing an angular passage of the upper and lower buttress straps through the pair of slots around the patella opening such that when the upper and lower buttress straps are pulled in an upward and downward criss-cross manner, the upper and lower buttress straps move closer and reduce a radius of the buttress.

6. The system of claim 1, wherein an inside surface of the patella stabilizer sleeve around a location on a circumferential edge of the patella opening is constructed of hook and pile portions to engage and facilitate adjustability of the buttress.

7. The system of claim 1, wherein a back side of the buttress is constructed of hook and pile portions to engage with hook and pile portions on the inside surface of the patella stabilizer sleeve around the location on the circumferential edge of the patella opening.

8. The system of claim 1, wherein a front side of the buttress is constructed of a material having anti-slip characteristics.

9. The system of claim 1, wherein the front side of the buttress is constructed of shark-skin material.

10. The system of claim 1, wherein the buttress is positioned in a medial direction relative to the user's patella.

11. The system of claim 1, wherein the buttress is positioned in a lateral direction relative to the user's patella.

12. The unitary knee patella stabilizer of claim 1, wherein the buttress is adapted to properly align the user's patella.

13. The system of claim 1, wherein the buttress is adapted to vary compression around the user's patella by increasing or decreasing tightness of the upper and lower buttress straps.

14. The system of claim 1, wherein the fasteners comprise hook and loop.

15. The system of claim 1, wherein the patella stabilizer sleeve further comprises:
   a first hinge placed along a medial portion of the patella stabilizer sleeve; and
   a second hinge placed opposite the first hinge.

16. The system of claim 1, wherein the buttress is horseshoe like in shape.

17. The system of claim 1, wherein the patella stabilizer sleeve is constructed of sufficient material to encompass thigh and calf regions at least once.

18. A unitary hinged knee support apparatus adapted to accommodate a leg portion of a user, the apparatus comprising:
   a sleeve extended at both ends into a plurality of straps;
   a patella opening;
   an upper fastener assembly having an upper inner strap extended from a first upper end of the apparatus and an upper outer strap extended from a second upper end of the apparatus, the upper outer strap having a fastener at a distal end;
   a lower fastener assembly having a lower inner strap extended from a first lower end of the apparatus and a lower outer strap extended from a second lower end of the apparatus, the lower outer strap having a fastener at a distal end;
   a pair of slots extending substantially non-parallel to a patella opening;
   the apparatus adapted to receive a buttress comprising an upper strap and a lower strap, the buttress being adapted to be adjustably positioned on an inside surface of the apparatus around a location on a circumferential edge of the patella opening; and
   wherein the upper strap is operable to be pulled in a generally outward and downward direction causing an upper distal end of the buttress to move closer to the patella opening and the lower strap is operable to be pulled in a generally outward and upward direction causing a lower distal end of the buttress to move closer to the patella opening for properly aligning a user's patella.

19. A method for properly aligning a user's patella, the method comprising:
   providing a unitary patella stabilizer sleeve having an upper fastener assembly comprising a first inner strap and a first outer strap and a lower fastener assembly comprising a second inner strap and a second outer strap;
   wrapping the inner straps around a back portion of a knee;
   wrapping the outer straps over the inner straps and around to a front portion of the knee;
   securing, via the first inner and outer straps of the upper fastener assembly, a thigh region of the user;
   securing, via the second inner and outer straps of the lower fastener assembly, a calf region of the user;
   adjustably positioning, on an inside surface of the patella stabilizer around a location on a circumferential edge of a patella opening, a buttress comprising an upper strap and a lower strap;
   a pair of slots extending substantially non-parallel to the patella opening, pulling the upper strap in a generally outward and downward direction causing an upper distal end of the buttress to move closer to the patella opening; and
   pulling the lower strap in a generally outward and upward direction causing a lower distal end of the buttress to move closer to the patella opening for varying compression and properly aligning a user's patella.

\* \* \* \* \*